United States Patent [19]

Reichwein et al.

[11] Patent Number: 5,939,553
[45] Date of Patent: Aug. 17, 1999

[54] PROCESS FOR PREPARING PYRIDINE-2,6-DIAMINES

[75] Inventors: Adrianus Maria Reichwein, Arnhem; Doetze Jakob Sikkema, Oosterbeek, both of Netherlands

[73] Assignee: Akzo Nobel N.V., Netherlands

[21] Appl. No.: 08/952,788

[22] PCT Filed: Apr. 24, 1996

[86] PCT No.: PCT/EP96/01730

§ 371 Date: Nov. 13, 1997

§ 102(e) Date: Nov. 13, 1997

[87] PCT Pub. No.: WO96/36607

PCT Pub. Date: Nov. 21, 1996

[30] Foreign Application Priority Data

May 15, 1995 [NL] Netherlands ............ 1000360

[51] Int. Cl.⁶ .............. C07D 213/09; C07D 213/73
[52] U.S. Cl. .............................. 546/250; 546/307
[58] Field of Search ....................... 546/250, 307

[56] References Cited

U.S. PATENT DOCUMENTS 3,225,041  12/1965  Johnson .................... 544/82
3,247,214   4/1966  Johnson .................... 546/297

FOREIGN PATENT DOCUMENTS 098684      1/1984  European Pat. Off. .
WO 94/25506 1/1994  WIPO .

OTHER PUBLICATIONS

J. Bernstein et al., "II. Derivatives of 2, 6–Diaminopyridine", Journal of the American Chemical Society, vol. 69, May 1947, pp. 1151–1155.

H.J. Den Hertog et al., "On the Reactivity of Bromine Atoms in Brominated pyridines. Preparation of Some 2:6–Disubstituted Products of Pyridine", Recueil des Travaux Chimiques des Pays–Bas, vol. 55, 1936, pp. 122–130.

K. Inuzuka et al., "The Amino–Imino Tautomerization of 2,6–Diaminopyridine by Interaction with Ethanol".

*Primary Examiner*—Alan L. Rotman
*Attorney, Agent, or Firm*—Richard P. Fennelly

[57] ABSTRACT

A process has been found for preparing pyridine-2,6-diamines, i.e., 2,6-diaminopyridine (DAP) and derivative compounds in which one of the amino groups is a substituted amine (secondary or tertiary). According to this process, 3-hydroxy pentane 1,5-dinitrile (3-hydroxyglutaronitrile) is reacted with an ammonium donor in the form of ammonia, a primary amine such as n-butylamine, or a secondary amine such as piperidine.

10 Claims, No Drawings

PROCESS FOR PREPARING PYRIDINE-2,6-DIAMINES

The invention pertains to a process for preparing pyridine-2,6-diamines having at least one primary amino (—NH$_2$) group, i.e., 2,6-diaminopyridine (DAP) and derivative compounds in which one of the amino groups is a substituted amine (secondary or tertiary).

DAP is a suitable starting material for preparing monomers for rigid rod polymers such as described in WO 94/25506, for dyes, metal ligands, medicines, and pesticides. It is well-known to prepare DAP by means of the Chichibabin reaction, in which pyridine is reacted with sodium amide. This is a complicated reaction requiring fairly severe conditions (e.g., 200° C. at increased pressure). Moreover, the reaction is not economical, since the comparatively expensive sodium amide has to be used in excess amount to counteract dimerisation. Furthermore, it is not known to synthesise monosubstituted DAP (having one secondary amino group), which would in any case be a complex process if the Chichibabin reaction were used.

It is known from U.S. Pat. No. 3,225,041 to prepare 2,6-diamino pyridines in which both amino groups are secondary or tertiary amines. This reaction involves contacting 3-hydroxy glutaronitrile with an excess of a primary or secondary amine, in the presence of a halogen acid (hydrogen halide). The disclosure does not pertain to the synthesis of pyridine-2,6-diamines having at least one primary amino group.

The invention has for its object to provide a simple, economically advantageous method of preparing unsubstituted DAP. It is further envisaged to provide a method by means of which derivatives of DAP can be made in which one of the amino groups is a substituted amine.

To this end the invention consists of a process for preparing pyridine-2,6-diamines having at least one primary amino group in which 3-hydroxy pentane 1,5-dinitrile (3-hydroxyglutaronitrile) is reacted with an ammonium donor in the form of ammonia, a primary or a secondary amine, with the proviso that if the ammonium donor is a primary or secondary amine, the use of hydrogen halide as a catalyst is refrained from.

Thus, in one embodiment, the invention is a process for preparing pyridine-2,6-diamine wherein 3-hydroxy pentane 1,5-dinitrile is reacted with ammonia. In another embodiment, the invention is a process for preparing pyridine-2,6-diamines having one primary and one secondary or tertiary amino group, wherein 3-hydroxy pentane 1.5-dinitrile is reacted with a primary or secondary amine in the substantial absence of hydrogen halide.

The starting material, 3-hydroxy pentane 1,5-dinitrile, can be synthesised by reacting epichlorohydrin with sodium cyanide in aqueous solution at pH 8–10. This pH can be set, e.g., by buffering with magnesium sulphate heptahydrate (MgSO$_4$.7H$_2$O) in a known manner. The desired dinitrile is obtained in a yield of about 60% via this process. According to the invention, it was found that a higher yield, 80%, can be obtained if, instead of the magnesium sulphate buffer, a pH electrode coupled to an automatic burette is employed and hydrochloric acid (or, as the case may be, caustic soda) is added during the reaction in this manner, and the reaction temperature is carefully controlled in the range of 20° to 35° C. Instead of hydrochloric acid, sulphuric acid may be used. In a preferred way to carry out this reaction, epichlorohydrin, sodium cyanide solution and sulphuric acid are dropwise added simultaneously. By thus avoiding the presence of all of the sodium cyanide in the reaction vessel, a lower amount of HCN is present during the reaction, which is safer and which leads to avoiding HCN induced by-product formation. Further, the reaction can be controlled better.

The preparation of DAP by the ring closure reaction of 3-hydroxy pentane 1,5-dinitrile and ammonia can be depicted as follows:

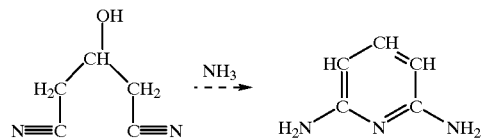

The reaction is carried out in a solvent, at room temperature or above, and preferably at elevated temperature (100–200° C., most preferably 140–160° C.). The molar ratio of ammonium donor to 3-hydroxy pentane 1,5-dinitrile is at least 1:1, preferably between 1:1 and 3:1, most preferably about 2:1. Suitable solvents include alcohols such as methanol, ethanol, propanol, and glycols. The reaction yield in the process according to the invention was found to be surprisingly high, i.e., 95%.

Alternatively, the ring closure reaction can be carried out using ammonium donors other than ammonia. Ammonium donors have the general formula >NH, wherein the substituents on the nitrogen atom can represent hydrogen as well as aliphatic or aromatic or heterocyclic hydrocarbon groups, optionally also with other substituents resistant to the reaction conditions. Also, the nitrogen atom can be part of a cyclic amine. Examples of suitable ammonium donors are ammonia, aliphatic amines such as n-butylamine, substituted aliphatic amines such as benzylamine, cyclic amines such as piperazine, and aromatic amines such as aniline.

If the ammonium donor is a primary or secondary amine, novel asymmetric pyridine-2,6-diamines are obtained in which one of the amino groups is a primary amine while the other is the secondary or tertiary amine corresponding to the primary or secondary amine ammonium donor used. Generally, these compounds satisfy the formula:

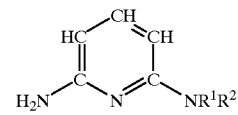

wherein R$^1$ represents hydrogen or R$^3$ and wherein R$^2$ and R$^3$ are the same or different and either each represent a separate aliphatic or aromatic hydrocarbon group, or together form an alicyclic or heterocyclic hydrocarbon ring. It is preferred that R$^2$, and if present R$^3$, are aliphatic hydrocarbon groups such as C$_1$ to C$_6$ alkyl, or phenyl. As an example, if the ring closure is conducted in the presence of n-butyl amine, the following compound is obtained:

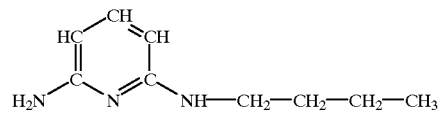

The ring closure is preferably performed in the presence of an appropriate catalyst, such as a transition metal or a transition metal ion activating a nitrile to be reacted. Examples of suitable catalysts are metallic copper, copper compounds (both monovalent and divalent copper salts), pre-eminently CuCl, $Cu_2O$ and $Cu(II)SO_4$, metallic cobalt, and Co(II) salts, manganese and Mn(II) salts, zinc and Zn(II) salts, and to some extent Fe(II) and Ca(II) salts. The catalyst is added in an amount of 0.1 to 20 mole %. The metallic copper, which is easy to recover, is preferably employed in a large quantity (20 wt. %). Copper(I)chloride and copper (II)sulphate are preferably employed in amounts of 2–4 wt. %. The catalyst serves to improve the yield in all cases, and most eminently in the case of the reaction with the primary and secondary amines.

Non-substituted 2,6-diaminopyridine is pre-eminently suited to be used as starting material for the preparation of 2,6-diamino-3,5 dinitropyridine, which is a precursor for the preparation of rigid rod polymers. Substituted, asymmetric pyridine-2,6-diamines are pre-eminently suited to be used as starting material for the production of pharmaceuticals (analgesic effect, inflammation inhibiting), bactericidal agents, and products for the dye industry. For instance, pyridium (phenazopyridine) is known as a remedy for bladder and urinary passages problems. A wide range of derivatives is described in *JACS* 65 (1943), 2241–2243.

The invention will be further illustrated with reference to the following unlimitative examples.

EXAMPLE 1
[Synthesis of 3-hydroxyglutaronitrile]

61.74 g of sodium cyanide (1.26 moles) were dissolved in 160 ml of water at 20° C. With the aid of a pH-stat the pH was set at 10.0 by adding 6 M hydrochloric acid. On conclusion of the hydrochloric acid addition 55.5 of epichlorohydrin (0.60 mole) were added dropwise at 20° C., with the burette starting to add hydrochloric acid again to keep the pH at a constant level. Some time after the epichlorohydrin addition had been concluded the pH began to drop. The pH-stat was then connected to a burette containing 6 M caustic soda, and the temperature was increased to 30° C. After about nine hours the reaction came to an end and the reaction mixture was neutralised. The product was isolated by continuous extraction with ethyl acetate, the yield being about 80%. The product can be purified by vacuum distillation.

EXAMPLE 2
[Cyclisation of 3-HGN to DAP]

A mixture of 5.99 g of 3-hydroxyglutaronitrile (54.5 mmoles), 3.25 g of $NH_3$ (191 mmoles), and 15.0 g of methanol was heated to 150° C. in an autoclave for three hours. After the reaction mixture had been cooled down and filtered, the solvent was evaporated in vacuo, with the crude DAP being left behind as a solid. The yield of the crude product is over 95%. According to $^1$H-NMR spectroscopy, this crude product contained approximately 42% of the starting material 3-HGN, and 58% of DAP. The product, which thus has an overall yield of 55.1%, can be purified by crystallisation from water as the sulphate salt or through vacuum distillation.

EXAMPLE 3
(a) [Cyclisation of 3-HGN to DAP using CuCl]

A mixture of 5.0 g of 3-hydroxyglutaronitrile (45.5 mmoles), 2.3 g of $NH_3$ (135 mmoles), 0.2 g of copper(I) chloride (2.0 mmoles), and 15.0 g of methanol was heated to 150° C. in an autoclave for three hours. After the reaction mixture had been cooled down and filtered, the solvent was evaporated in vacuo, with the crude DAP being left behind as a solid in a yield of over 95% (DAP only, no starting material left.

Analogously, by heating to 150° C. in 15.0 g of methanol in an autoclave for 3 hours, the cyclisation of 3-HGN to DAP was conducted using the following reactants and catalysts:

(b) 5,52 g of 3-hydroxyglutaronitrile (50.2 mmoles), 3.25 g of $NH_3$ (191 mmoles), and 0.14 g of copper(I)oxide; Yield 95% of DAP.

(c) 5.54 g of 3-hydroxyglutaronitrile (50.4 mmoles), 3.25 g of $NH_3$ (191 mmoles), and 0.50 g of cobalt(II) acetate tetrahydrate, $Co(OAC)_2.4H2O$ (2.0 mmoles); Yield: 95% of DAP.

(d) 5,58 g of 3-hydroxyglutaronitrile (50.7 mmoles), 3.25 g of $NH_3$ (191 mmoles), and 0.51 g of manganese (II) acetate tetrahydrate, $Mn(OAC)_2.4H2O$ (2.1 mmoles); Yield: 95% of DAP.

(e) 5.64 g of 3-hydroxyglutaronitrile (51.3 mmoles), 3.25 g of $NH_3$ (191 mmoles), and 0.27 g of zinc(II)chloride, $ZnCl_2$ (2.0 mmoles); Yield: 91.2% of DAP.

(f) 5.53 g of 3-hydroxyglutaronitrile (50.3 mmoles), 3.25 g of $NH_3$ (191 mmoles), and 0.56 g of iron(II)sulphate heptahydrate, $FeSO_4.7H_2O$ (2.0 mmoles); Yield: 72.2% of DAP.

(g) 5,52 g of 3-hydroxyglutaronitrile (50.2 mmoles), 3.25 g of $NH_3$ (191 mmoles), and 0.30 g of calcium chloride, $CaCl_2.2H_2O$. Yield: 66.5% of DAP.

EXAMPLE 4
[Cyclisation of 3-HGN using dimethylamine]

A mixture of 5.05 g of 3-hydroxyglutaronitrile (45.9 mmoles), 3.41 g of dimethylamine (76 mmoles), 0.30 g of copper(I)chloride (3.0 mmoles), and 11.8 g of methanol was heated to 160° C. in an autoclave for three hours. After the reaction mixture had been cooled down and filtered, the solvent was evaporated in vacuo, with the crude product left behind as an oil in a yield of 95%. According to $^1$H-NMR spectroscopy, the product contained 47.4% of 2-amino-6-N, N-dimethylamino pyridine which was isolated in pure form from the by-products 2,6-N,N,N',N'-tetramethyldiamino pyridine and 2,6-diaminopyridine using column chromatography (silica, 1:2 ethyl acetate/hexane).

EXAMPLE 5
[Cyclisation of 3-HGN using piperidine]

A mixture of 5.11 g of 3-hydroxyglutaronitrile (46.5 mmoles), 4.07 g of piperidine (47.8 mmoles), 0.30 g CuCl (3.0 mmoles), and 15.0 g of methanol was heated to 160° C. in an autoclave for three hours. After the reaction mixture had been cooled down and filtered, the solvent was evaporated in vacuo, with the crude product being left behind in the form of an oil in a yield of 88%. According to $^1$H-NMR spectroscopy the product contained 63.3% of 2-amino-6-N-piperidino pyridine.

EXAMPLE 6
[Cyclisation of 3-HGN using n-butylamine]

A mixture of 5.0 g of 3-hydroxyglutaronitrile (45.5 mmoles), 3.7 g of n-butylamine (50.7 mmoles), 0.2 9 of copper(I)chloride (2.0 mmoles), and 15.0 g of methanol was heated to 150° C. in an autoclave for three hours. After the reaction mixture had been cooled down and filtered, the solvent was evaporated in vacuo, with the crude N-butyl-2, 6-diamino pyridine (confirmed by $^1$H-NMR spectroscopy) being left behind in the form of an oil.

EXAMPLE 7
[Cyclisation of 3-HGN using aniline]

A mixture of 5.06 g of 3-hydroxyglutaronitrile (46.0 mmoles), 6.32 g of aniline (68 mmoles), 0.30 g CuCl (3.0 mmoles), and 15.0 g of methanol was heated to 160° C. in an autoclave for three hours. After the reaction mixture had been cooled down and filtered, the solvent was evaporated in vacuo, with the crude 2-amino-6-N-anilino pyridine (confirmed by $^1$H-NMR spectroscopy) being left behind in the form of an oil.

We claim:

1. A process for preparing pyridine-2,6-diamine compounds having at least one primary amino group, wherein 3-hydroxy pentane 1,5-dinitrile is reacted with an ammonium donor in the form of ammonia, a primary amine or a secondary amine, with the proviso that if the ammonium donor is a primary or secondary amine, the use of hydrogen halide as a catalyst is refrained from.

2. A process for preparing pyridine-2,6-diamine according to claim 1, comprising reacting 3-hydroxy pentane 1,5-dinitrile with ammonia.

3. A process according to claim 1 or 2, wherein the reaction is carried out in a suitable solvent at a temperature of 100–200° C.

4. A process according to claims 1 or 2, wherein the reaction is carried out in the presence of a nitrile-activating catalyst comprising a Ca(II) salt or a transition metal or a transition metal ion selected from metallic copper cobalt, manganese, and zinc, and the monovalent and divalent salts of copper, and the divalent salts of cobalt, manganeeme, zinc, or iron.

5. A process according to claim 4, wherein the catalyst employed is metallic copper, a copper (I) or a copper (II) compound.

6. A process for preparing a substituted pyridine-2,6-diamine according to claim 1, wherein 3-hydroxy pentane 1,5-dinitrile is subjected to ring closure by contacting it with a primary or secondary amine, the ring closure being effected in the substantial absence of hydrogen halide.

7. A process according to claim 6, wherein the amine is selected from the group consisting of aliphatic primary amines, aliphatic secondary amines, alicyclic amines, and mixtures thereof.

8. A process according to claims 6 or 7, wherein the reaction is carried out in the presence of a nitrile-activating catalyst comprising a Ca(II) salt or a transition metal or a transition metal ion selected from metalic copper, cobalt, manganese and zinc, and the monovalent and divalent salts of copper, and the divalent salts of cobalt, manganese, zinc, or iron.

9. A process according to claim 8, wherein the catalyst employed is metallic copper, copper (I) or a copper (II) compound.

10. A process according to claim 3, characterised in that the reaction is carried out in the presence of a nitrile-activating catalyst comprising a transition metal or a transition metal ion.

* * * * *